(12) United States Patent
Gyrn

(10) Patent No.: US 11,957,871 B2
(45) Date of Patent: *Apr. 16, 2024

(54) COATED SUBCUTANEOUS DEVICE AND INSERTER SYSTEM

(71) Applicant: UNOMEDICAL A/S, Birkerød (DK)

(72) Inventor: Steffen Gyrn, Ringsted (DK)

(73) Assignee: UNOMEDICAL A/S, Lejre (DK)

(*) Notice: Subject to any disclaimer, the term of this patent is extended or adjusted under 35 U.S.C. 154(b) by 580 days.

This patent is subject to a terminal disclaimer.

(21) Appl. No.: 17/088,214

(22) Filed: Nov. 3, 2020

(65) Prior Publication Data
US 2021/0046242 A1 Feb. 18, 2021

Related U.S. Application Data

(63) Continuation-in-part of application No. 16/121,902, filed on Sep. 5, 2018, now Pat. No. 10,898,644, which
(Continued)

(51) Int. Cl.
A61M 5/158 (2006.01)
A61M 25/00 (2006.01)
A61M 25/06 (2006.01)

(52) U.S. Cl.
CPC ........ A61M 5/158 (2013.01); A61M 25/0045 (2013.01); A61M 25/0097 (2013.01);
(Continued)

(58) Field of Classification Search
CPC .... A61B 2560/063; A61M 2005/1583; A61M 2005/1585; A61M 2005/1586;
(Continued)

(56) References Cited

U.S. PATENT DOCUMENTS 4,755,173 A * 7/1988 Konopka .......... A61M 25/0606
604/122
5,851,197 A 12/1998 Marano et al.
(Continued)

FOREIGN PATENT DOCUMENTS

EP 1011785 B1 1/2007
EP 1846064 B1 6/2009
(Continued)

Primary Examiner — Shefali D Patel
(74) Attorney, Agent, or Firm — Taft Stettinius & Hollister LLP; Ryan O. White; Derek B. Lavender

(57) ABSTRACT

A medical device having an antimicrobial coating on a surface of the medical device and an inserter device for subcutaneously inserting the medical device. The inserter device includes an outer part having one or more locking elements including a first locking element and one or more release elements including a first release element; a housing; and a functional part accommodated in the housing. The housing includes a sidewall with an inner surface forming a cavity, the housing extending from a first end to a second end along a first axis and comprising one or more housing guide members including a first housing guide member for engagement with one or more guide members of the functional part. The functional part comprises a first part with a first body extending from a first end to a second end along the first axis.

17 Claims, 11 Drawing Sheets

Related U.S. Application Data is a continuation of application No. 14/008,483, filed as application No. PCT/EP2012/055803 on Mar. 30, 2012, now Pat. No. 10,076,607.

(60) Provisional application No. 61/469,406, filed on Mar. 30, 2011.

(52) U.S. Cl.
CPC .... *A61M 25/0606* (2013.01); *A61M 25/0612* (2013.01); *A61M 25/0631* (2013.01); *A61B 2560/063* (2013.01); *A61M 2005/1583* (2013.01); *A61M 2005/1585* (2013.01); *A61M 2005/1586* (2013.01); *A61M 2205/0205* (2013.01); *A61M 2205/0238* (2013.01)

(58) Field of Classification Search
CPC .. A61M 2025/0004; A61M 2025/0056; A61M 2025/0175; A61M 2205/0205; A61M 2205/0238; A61M 25/0045; A61M 25/0097; A61M 25/06; A61M 25/0606; A61M 25/0612; A61M 25/0631; A61M 25/065; A61M 5/158; A61M 25/02; A61M 2025/028

See application file for complete search history.

(56) References Cited

U.S. PATENT DOCUMENTS

| | | | |
|---|---|---|---|
| 6,093,172 A | 7/2000 | Funderburk et al. | |
| 6,451,003 B1 | 9/2002 | Prosl et al. | |
| 6,607,509 B2 | 8/2003 | Bobroff et al. | |
| 6,997,907 B2 | 2/2006 | Safabash et al. | |
| 7,207,974 B2 | 4/2007 | Safabash et al. | |
| 7,318,816 B2 | 1/2008 | Bobroff et al. | |
| 7,585,287 B2 | 9/2009 | Bresina et al. | |
| 7,699,807 B2 | 4/2010 | Faust et al. | |
| 7,704,229 B2 | 4/2010 | Moberg et al. | |
| 7,731,691 B2 | 6/2010 | Cote et al. | |
| 7,879,010 B2 | 2/2011 | Hunn et al. | |
| 8,070,722 B2 | 12/2011 | Moberg et al. | |
| 8,292,849 B2 | 10/2012 | Bobroff et al. | |
| 8,394,058 B2 | 3/2013 | Moberg et al. | |
| 8,409,145 B2 | 4/2013 | Raymond et al. | |
| 8,414,529 B2 | 4/2013 | Moberg et al. | |
| 8,469,929 B2 | 6/2013 | Hunn et al. | |
| 8,545,443 B2 | 10/2013 | Moberg et al. | |
| 8,628,498 B2 | 1/2014 | Safabash et al. | |
| 8,641,674 B2 | 2/2014 | Bobroff et al. | |
| 8,801,660 B2 | 8/2014 | Hunn et al. | |
| 9,181,401 B2 * | 11/2015 | Parakka | A61L 15/26 |
| 9,186,438 B2 | 11/2015 | Gravesen et al. | |
| 10,058,638 B2 | 8/2018 | Gravesen et al. | |
| 11,027,060 B2 | 6/2021 | Chiu et al. | |
| 11,027,061 B2 | 6/2021 | Chiu et al. | |
| 2002/0072720 A1 * | 6/2002 | Hague | A61M 5/32 |
| | | | 604/264 |
| 2003/0199823 A1 | 10/2003 | Bobroff et al. | |
| 2007/0003603 A1 | 1/2007 | Karandikar et al. | |
| 2007/0129690 A1 * | 6/2007 | Rosenblatt | A61P 31/04 |
| | | | 424/422 |
| 2007/0156094 A1 | 7/2007 | Safabash et al. | |
| 2009/0264825 A1 | 10/2009 | Cote et al. | |
| 2009/0287153 A1 | 11/2009 | Bresina et al. | |
| 2010/0030155 A1 | 2/2010 | Gyrn et al. | |
| 2011/0060287 A1 | 3/2011 | Ambruzs et al. | |
| 2011/0257597 A1 | 10/2011 | Safabash et al. | |
| 2012/0035549 A1 | 2/2012 | Moberg et al. | |
| 2012/0059322 A1 | 3/2012 | Moberg et al. | |
| 2012/0130315 A1 * | 5/2012 | Weadock | A61M 25/02 |
| | | | 604/174 |
| 2012/0179106 A1 | 7/2012 | Cote et al. | |
| 2013/0060233 A1 | 3/2013 | O'Connor et al. | |
| 2013/0102965 A1 | 4/2013 | Teutsch et al. | |
| 2013/0138078 A1 | 5/2013 | Smith et al. | |
| 2013/0281931 A1 | 10/2013 | Hunn et al. | |
| 2013/0345635 A1 | 12/2013 | Moberg et al. | |
| 2014/0039458 A1 | 2/2014 | Constantineau et al. | |
| 2016/0243302 A1 * | 8/2016 | Gyrn | A61M 5/158 |
| 2019/0217023 A1 | 7/2019 | Chattaraj et al. | |
| 2021/0178074 A1 | 6/2021 | Anderson et al. | |
| 2021/0268180 A1 | 9/2021 | Chiu et al. | |
| 2022/0031941 A1 | 2/2022 | Dang et al. | |

FOREIGN PATENT DOCUMENTS

| | | |
|---|---|---|
| EP | 1044028 B2 | 1/2010 |
| EP | 2201969 B1 | 3/2011 |
| EP | 2380620 A2 | 10/2011 |
| EP | 2383011 A2 | 11/2011 |
| EP | 1743667 B1 | 2/2012 |
| EP | 2535064 A1 | 12/2012 |
| EP | 2596821 A1 | 5/2013 |
| EP | 1691877 B1 | 12/2013 |
| EP | 1389138 B1 | 8/2016 |
| EP | 1383560 B1 | 11/2016 |
| EP | 1684840 B1 | 10/2017 |
| EP | 2231231 B1 | 3/2019 |
| EP | 2673035 B1 | 4/2020 |
| WO | 2002081012 A2 | 10/2002 |
| WO | 2008029280 A2 | 3/2008 |
| WO | 2009039013 A1 | 3/2009 |
| WO | 2012141759 A1 | 10/2012 |

* cited by examiner

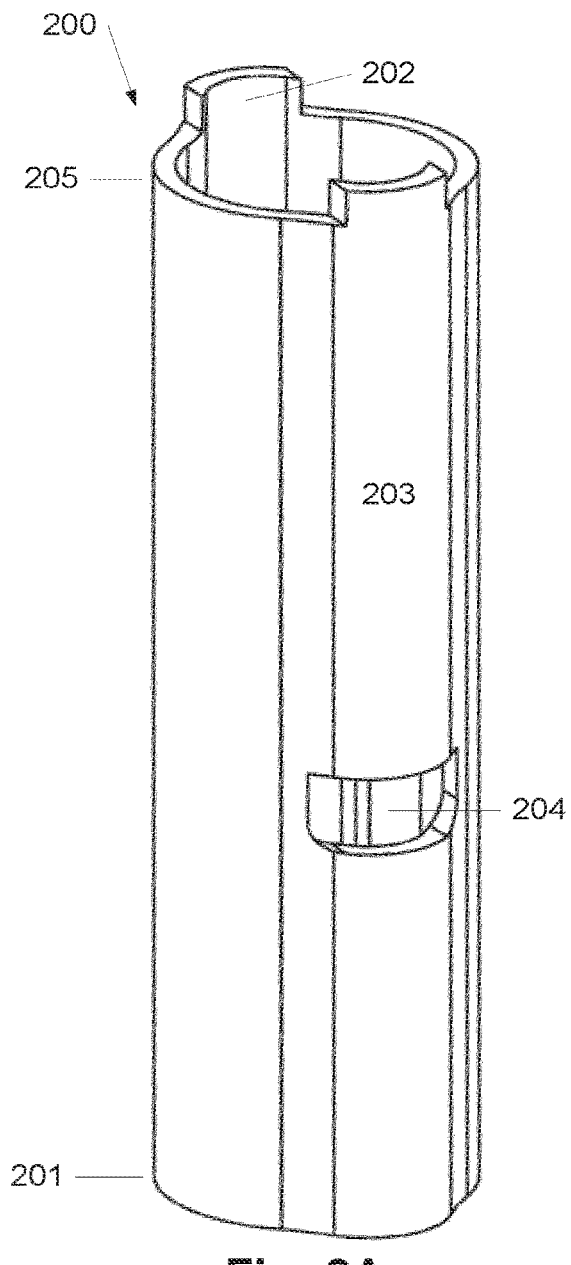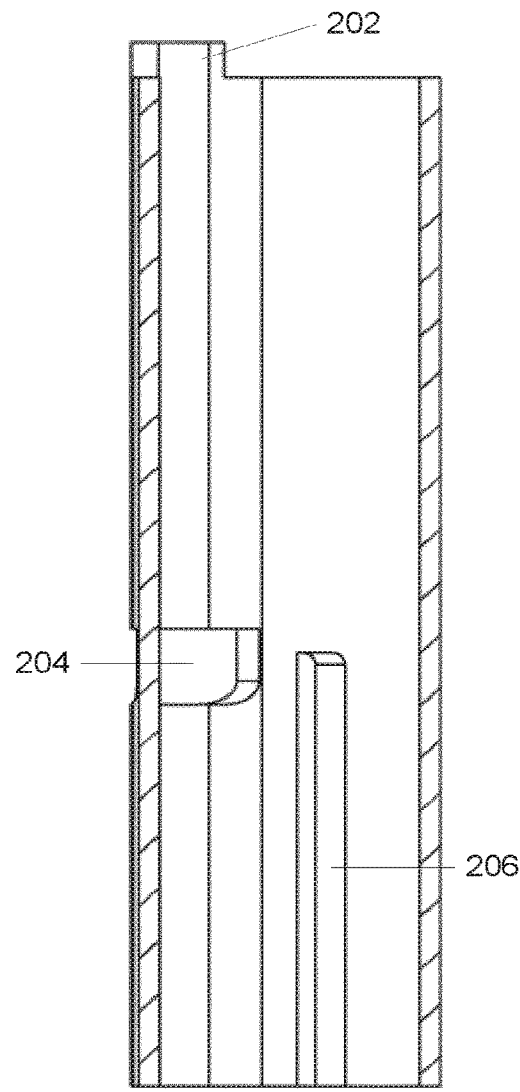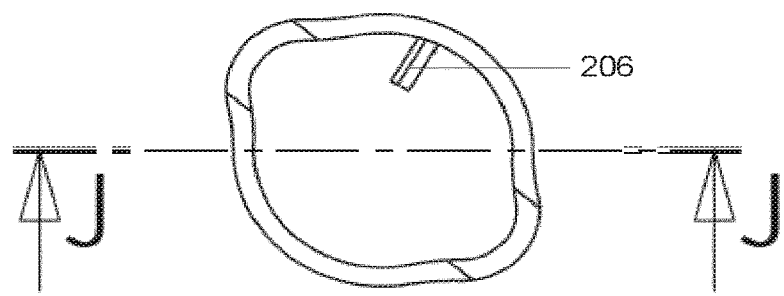
Fig. 2A
Fig. 2B
Fig. 2C

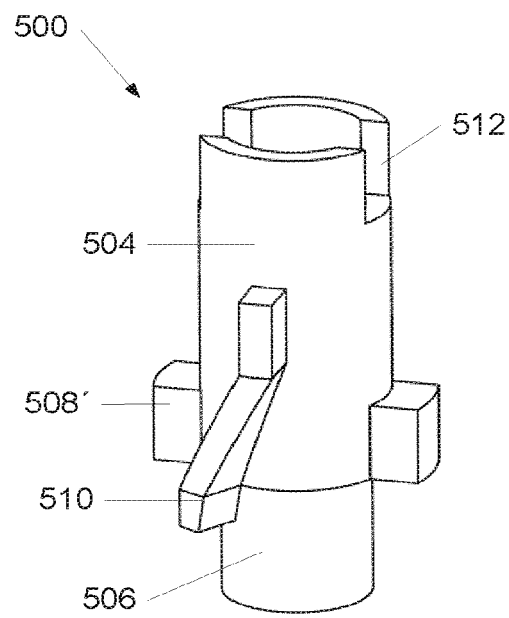
Fig. 5A
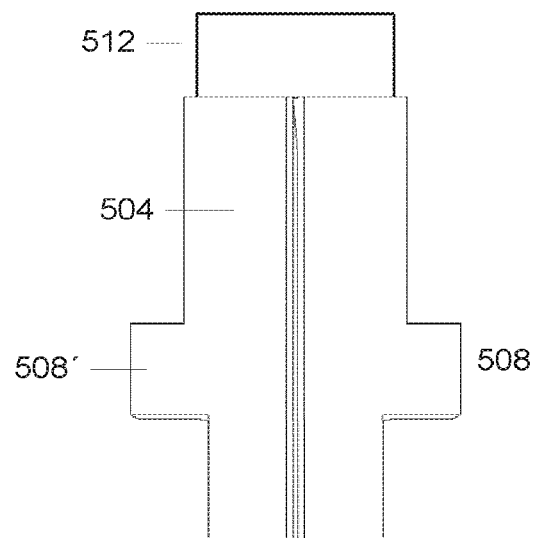
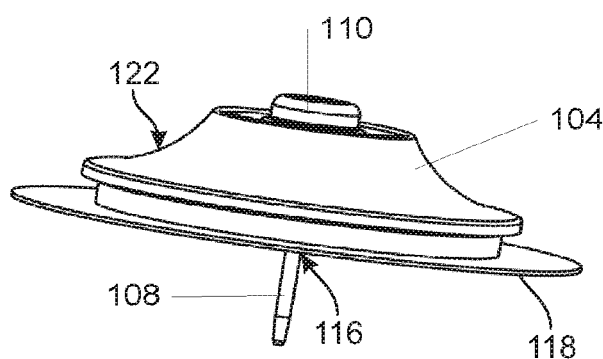
Fig. 6
Fig. 5B

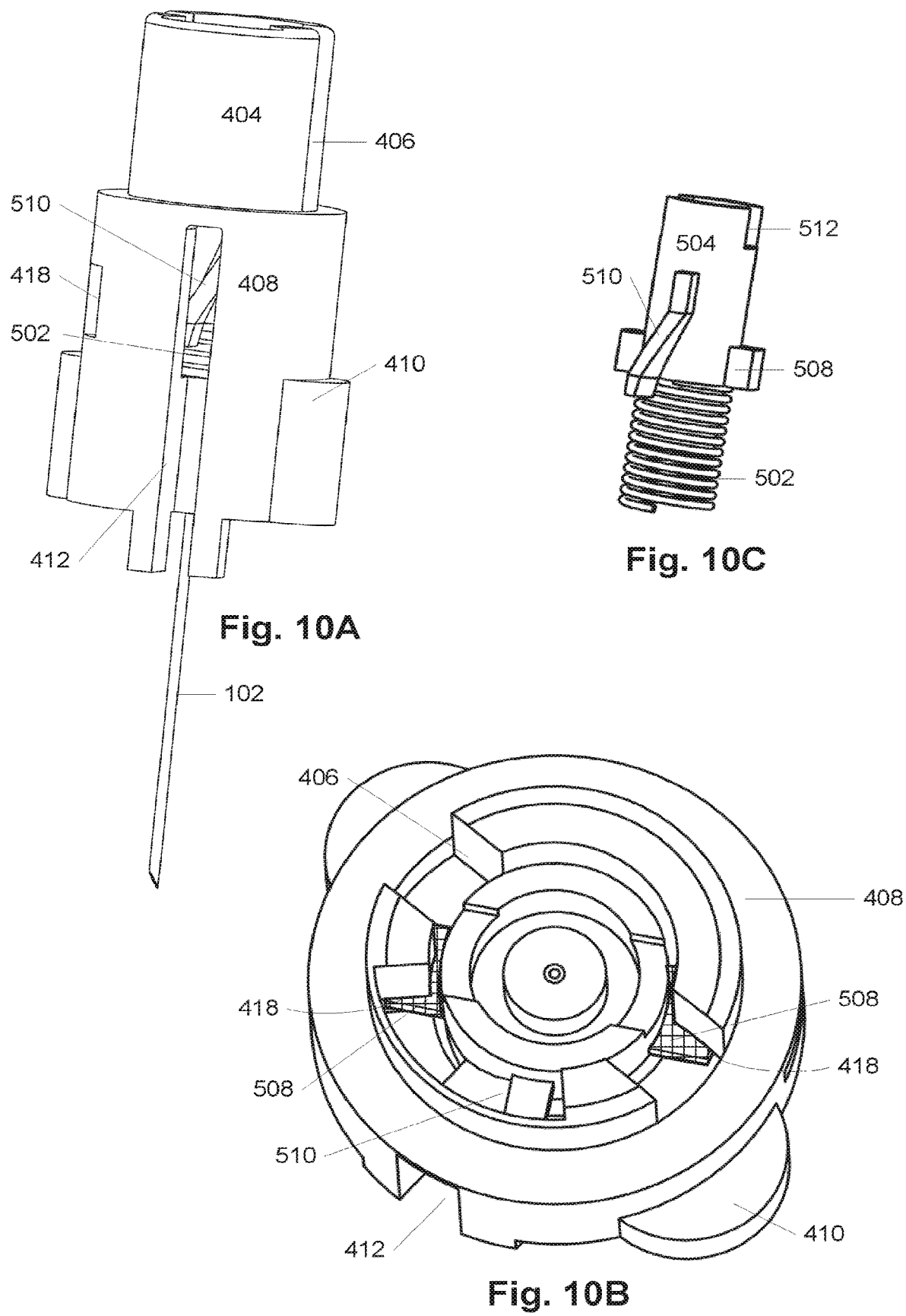

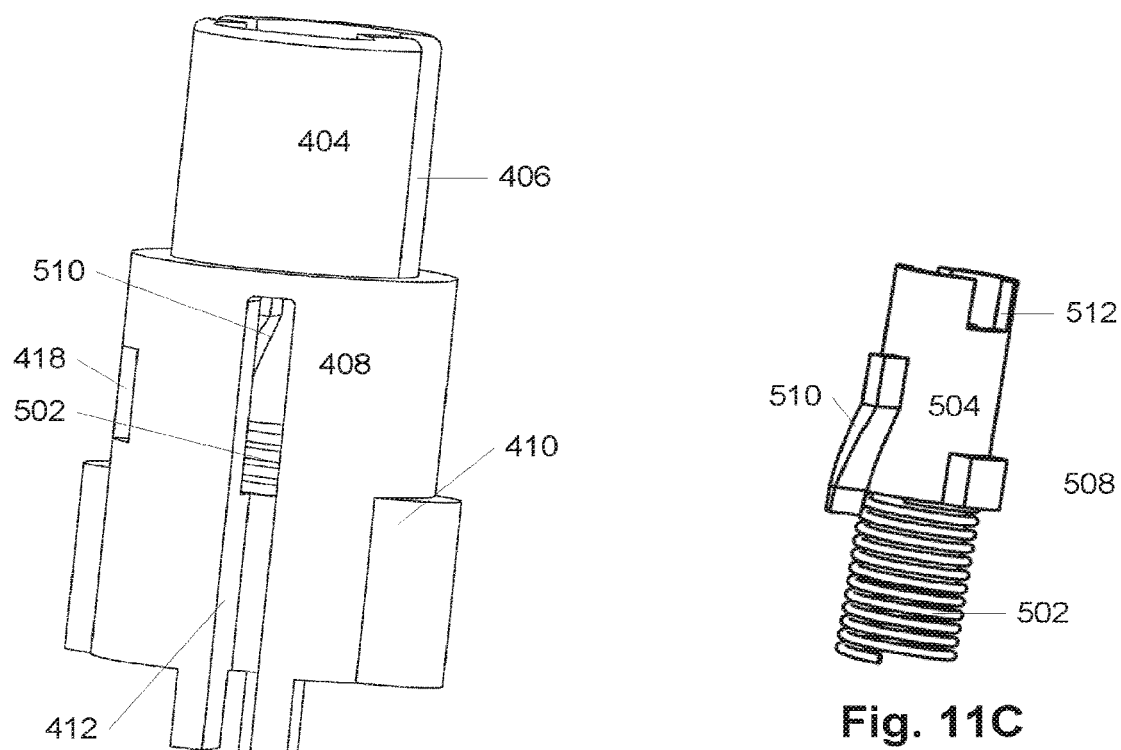
Fig. 11A
Fig. 11C
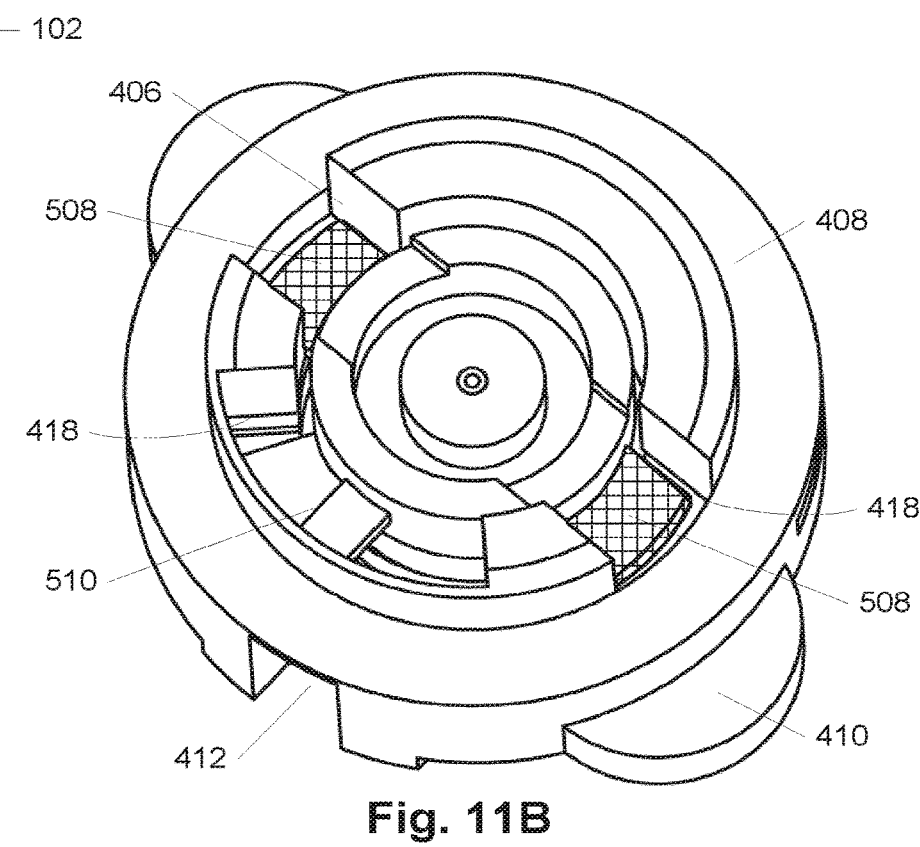
Fig. 11B

COATED SUBCUTANEOUS DEVICE AND INSERTER SYSTEM

CROSS-REFERENCE

This application is a continuation-in-part of U.S. application Ser. No. 16/121,902, filed Sep. 5, 2018, which is a continuation of U.S. application Ser. No. 14/008,483, filed Feb. 5, 2016, now issued as U.S. Pat. No. 10,076,607 on Sep. 18, 2018, which is the National Stage Entry of International Application No. PCT/EP2012/055803, filed Mar. 30, 2012, which claims priority to U.S. Provisional Application No. 61/469,406, filed on Mar. 30, 2011, all of which are incorporated herein by reference in their entireties.

FIELD OF THE DISCLOSURE

The present disclosure relates to an inserter device for inserting a medical device subcutaneously comprising an outer part, a housing, and a functional part.

BACKGROUND OF THE DISCLOSURE

An inserter device also called inserter or injector is commonly used in the medical field for inserting medical devices, such as infusion sets, sensors or the like, through the skin of a patient in a more or less automated fashion.

Commonly, when using an inserter, the user, i.e. the patient or the treatment provider e.g. nurse, doctor, relative, or the like has to apply a force towards the surface of the skin of the patient in order to provide injection of the medical device or a part of the medical device having the form of a needle, a cannula, a sensor, or the like. This can cause physiological or psychological distress and/or discomfort, and may lead to inappropriate application of the medical device. Many people are afraid of sharp objects, such as injection needles and other penetrating devices, commonly used for medical treatment and therapy. This fear is often irrational, and it may hamper an appropriate medical treatment. For example, in the case of self-medication, a lack of administration of an appropriate dose of a required medical composition can lead to complications, which may even be life-threatening. When treating diabetes, e.g. in juveniles, there is a risk that the required insulin-dose may not be self-administered due to irrational fear of the insertion needle, combined with a general lack of knowledge and awareness concerning the consequences of omitting the correct application of the device and dosage.

A further known issue with insertion of medical devices is the risk of contamination of the penetrating member before or during application. This can easily lead to the introduction of an infection to a patient, e.g. through a contaminated insertion needle. The longer such a needle is exposed, the higher the risk of accidental contamination, e.g. by touching the needle with a finger, bringing the needle in contact with an unclean surface, or by airborne contamination, aerosol contamination and the like. Depending on the nature of the contamination (e.g. comprising virus, bacteria, fungus, yeast and/or prion) combined with the general health status of the patient, the resulting infection can rapidly turn into a life threatening situation.

It is well known that contact with an infected, used needle especially in hospital environments can be life-threatening, and the risk of accidental exposure to contaminated material in the form of a used insertion needle must be minimized. Thus, there is a need in the art for a robust, reliable, accurate, safe, hygienic, and user friendly inserter device, which addresses the issues discussed above.

Conventional inserter devices have a cannula and/or needle placed within a body section for insertion into the subcutaneous layer of skin. The cannula may remain in place for up to three days, or perhaps longer. It is believed that if the cannula remains in place longer than approximately three days in one location in the subcutaneous layer of skin, the patient's body will identify the cannula as a foreign body and respond by rejecting the cannula. It is believed that the rejection of the foreign body causes a reduction in absorption of any drug being administered through the cannula. As a result, it would be an advantage to provide a solution to allow for increasing the length of time it takes for a body to begin to reject the cannula.

A method to overcome reduced absorption of a drug may include making the medication easier to absorb by the body via a modification near to the pump, which is secured to the cannula. Such modification may be the type represented by the pump connector described in U.S. Application Publication No. 20190217023; however, such a modification will not slow down the body's response to the cannula. What is needed therefore is a cannula and related components which may remain non-detected by the patient's body while the cannula is subcutaneously inserted.

SUMMARY

In an illustrative embodiment of the present disclosure, an inserter system comprising: a medical device and an inserter device for subcutaneously inserting at least a portion of the medical device, the medical device comprising: a port site and a subcutaneous part securable to the port site; wherein at least one of the port site and the subcutaneous part include an antimicrobial coating positioned on a surface thereof, and the inserter device comprising: an outer part comprising one or more locking elements including a first locking element and one or more release elements including a first release element; a housing; and a functional part accommodated in the housing; wherein the housing comprises a sidewall with an inner surface forming a cavity, the housing extending from a first end to a second end along a first axis and comprising one or more housing guide members including a first housing guide member for engagement with one or more guide members of the functional part, and where the housing is at least partly covered by the outer part; wherein the functional part comprises: a first part with a first body extending from a first end to a second end along the first axis, the first part comprising one or more first locking members; a second part releasably connected to the first part and comprising a second body extending from a first end to a second end along the first axis, the second part comprising a second guide member and one or more second locking members; an insertion needle attached to the second part; an insertion spring adapted for moving the first part from a first position to a second position in an insertion direction along the first axis in relation to the housing; and a retraction spring adapted for moving the second part from the second position to a third position in an extraction direction along the first axis in relation to the housing; wherein the first housing guide member and the second guide member are configured for rotating the second part about the first axis when the first part is moved from the first position to the second position, whereby the second part is moved from a locked position to an unlocked position relative to the first part.

In some embodiments, the first locking element is two protrusions positioned on an annular engaging device extending inwards. In some embodiments, the first release element is two surfaces positioned on the annular engaging device. In some embodiments, the one or more first locking members are protrusions on an outer surface of the first part.

In some embodiments, the first housing guide member is a wall extending from the sidewall into the cavity of the housing. In some embodiments, the second guide member is an inclining sidewall extending outwardly from an outer surface of the second part. In some embodiments, the one or more second locking members are protrusions extending outwardly from an outer surface of the second part. In some embodiments, the outer part comprises an annular collar on an inside of the outer part; wherein the insertion spring at a first end encircles the annular collar; and wherein the insertion spring at a second end encircles an outer part of the first part. In some embodiments, the retraction spring at a second end encircles an outer part of the second part; and wherein the first part comprises an annular recess on an inside of the first part for supporting the retraction spring at a first end.

In some embodiments, the subcutaneous part is configured to be secured inside a cavity in the port site upon subcutaneous insertion of the medical device. In some embodiments, the first part when in the second position exercises a pressure on the subcutaneous part thereby locking the subcutaneous part inside the cavity of the port site. In some embodiments, the first part when the second part is in the third position exercises a pressure on the subcutaneous part thereby preventing the subcutaneous part from departing from the port site upon extraction of the insertion needle. In some embodiments, the first part when the second part is in the third position exercises a pressure on the subcutaneous part thereby preventing the subcutaneous part from departing from the port site upon extraction of the insertion needle.

In some embodiments, the antimicrobial coating comprises an amphiphilic phosphorylcholine polymer.

In some embodiments, the subcutaneous part includes: a body part configured to secure the subcutaneous part to the port site, and a cannula extending proximally from the body part. In some embodiments, the antimicrobial coating is positioned on at least one surface of the subcutaneous part. In some embodiments, the antimicrobial coating is positioned on at least one surface of the cannula. In some embodiments, the antimicrobial coating is positioned on at least one surface of the body part.

In some embodiments, the port site includes a proximal surface configured to contact a patient's skin when the medical device is subcutaneously inserted; and the antimicrobial coating is positioned on the proximal surface of the port site.

In some embodiments, an inserter system comprises: a medical device and an inserter device for subcutaneously inserting at least a portion of the medical device; the medical device includes an antimicrobial coating positioned on a surface thereof; and the inserter device comprises: an outer part comprising one or more locking elements including a first locking element and one or more release elements including a first release element; a housing; and a functional part accommodated in the housing; the housing comprises a sidewall with an inner surface forming a cavity, the housing extending from a first end to a second end along a first axis and comprising one or more housing guide members including a first housing guide member for engagement with one or more guide members of the functional part, and where the housing is at least partly covered by the outer part; the functional part comprises: a first part with a first body extending from a first end to a second end along the first axis, the first part comprising one or more first locking members; a second part releasably connected to the first part and comprising a second body extending from a first end to a second end along the first axis, the second part comprising a second guide member and one or more second locking members; an insertion needle attached to the second part; an insertion spring adapted for moving the first part from a first position to a second position in an insertion direction along the first axis in relation to the housing; and a retraction spring adapted for moving the second part from the second position to a third position in an extraction direction along the first axis in relation to the housing; the first housing guide member and the second guide member are configured for rotating the second part about the first axis when the first part is moved from the first position to the second position, whereby the second part is moved from a locked position to an unlocked position relative to the first part.

In some embodiments, the antimicrobial coating comprises an amphiphilic phosphorylcholine polymer.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein:

FIGS. 2A-C show the housing of the inserter device;

FIGS. 5A-B show the second part of the inserter device;

FIG. 6 shows an embodiment of a port site;

FIG. 10A-C show the first part and the second part in a interlocked position subsequent to insertion of an insertion needle; and FIGS. 11A-C show the first part and the second part of FIGS. 10A-C in an unlocked position immediate prior to retraction of the insertion needle.

DETAILED DESCRIPTION

The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure.

Figure 1:
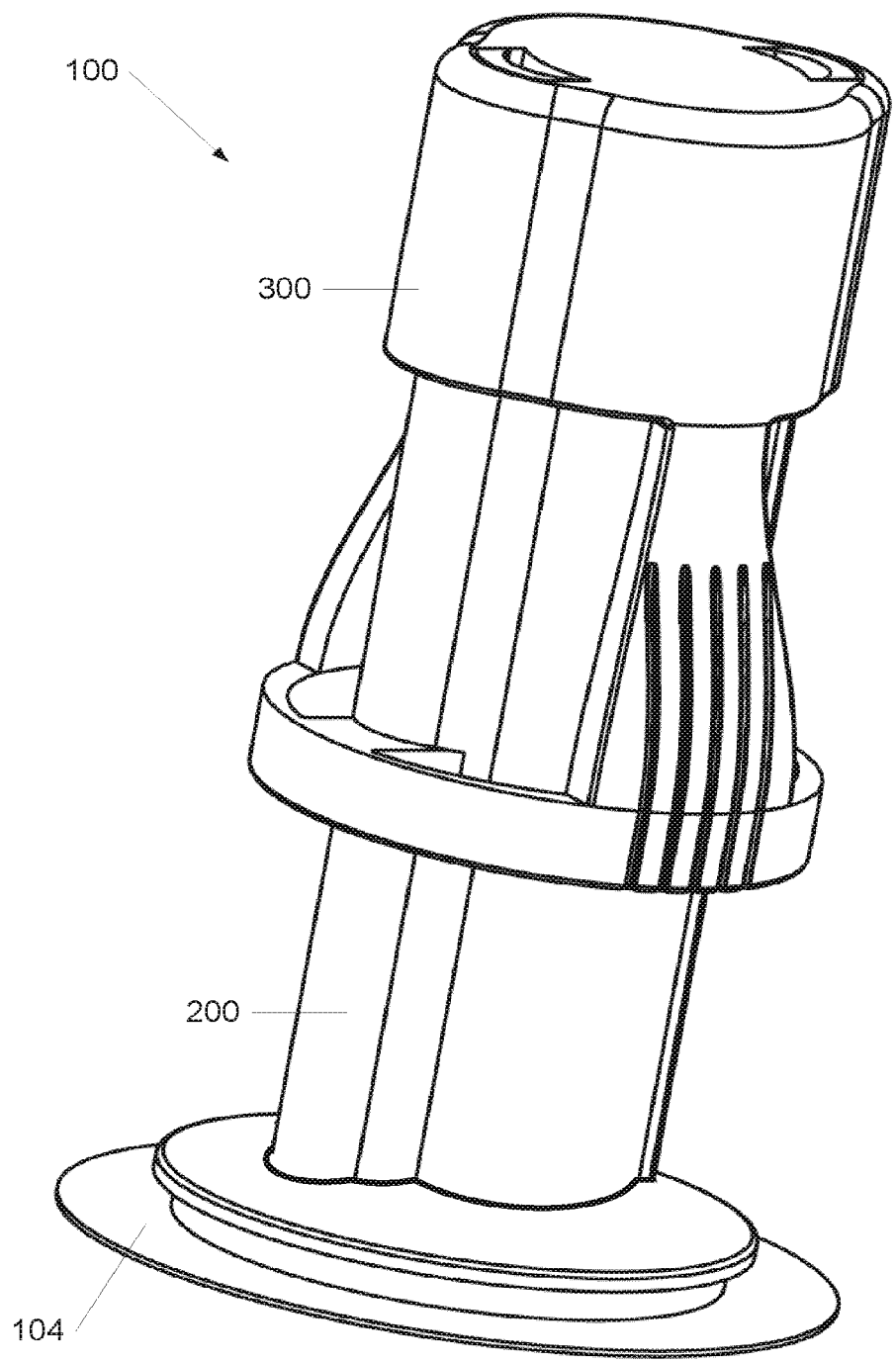
FIG. 1 shows the assembled inserter device.

FIG. 1 shows an embodiment of an inserter device 100 having automatic insertion and automatic retraction of an insertion needle 102. The inserter device 100 is used for placing a port site 104 combined with a subcutaneous part 106 (see FIGS. 7-9) subcutaneously in a patient. The port site 104 can be used for injecting portions of medication over a period of normally up to 3 days. The port site 104 can be e.g. an infusion device, a sensor device, patch devices or similar.

The inserter device 100 is displayed in FIG. 1 in an assembled shelf state and comprises an outer part 300 and a housing 200, where the housing 200 is partly covered by the outer part 300. Accommodated inside the housing 200 is a functional part which comprises: a first part 400; a second part 500; an insertion spring 402; a retraction spring 502; and an insertion needle 102 attached to the second part 500. The inserter part 100 is shown with a port site 104 being an infusion device attached, but other port sites could also be used. Throughout the description 'distal' will refer to the end/surface/element furthest away from the port site 104 and 'proximal' will refer to the end/surface/element closest to the port site 104. The 'vertical' plane/direction will refer to the plane/direction extending parallel with the insertion needle 102 and the 'horizontal' plane/direction will refer to the plane/direction parallel with the patient's skin surface, thus perpendicular to the vertical plane/direction.

FIG. 2A shows the housing 200 in a front view: FIG. 2B shows the housing 200 in a cut-through view along the axis J-J, and FIG. 2C shows the housing 200 in a view from the proximal end 201 of the housing 200. The shape and/or diameter of the proximal end 201 can have different designs depending on the site port 104 attached to the proximal end 201, and the invention is therefore not limited to the shown embodiment.

The housing 200 constitutes an elongated tube comprising a sidewall 203 with an inner surface forming a cavity. The housing 200 has in an oval shape ensuring that the first part 400 cannot rotate in the horizontal plane before, during or after activation of the insertion device 100.

The housing 200 comprises two proximal protrusions 202, which are positioned opposite one another at the distal end 205 of the housing 200. The proximal protrusions 202 are adapted for engaging with two corresponding openings 304 in the outer part 300. The housing 200 further comprises two openings 204, which are positioned horizontally opposite one another approximately in the middle of the housing 200. The openings 204 are adapted for engaging with locking elements 312 on the outer part 300. The proximal protrusions 202 and the openings 204 are aligned pair wise along vertical axes extending from the proximal end 203 to the distal end 205, thus extending in a direction parallel to the direction of insertion.

On the inside of the housing 200, there is a housing guide member 206 extending from proximal end 203 and to approximately the middle of the housing 200. The housing guide member 206 extends along an axis parallel to the axis defined by the pair wise proximal protrusions 202 and openings 204 displaced approximately 80-110 degrees in relation thereto. The housing guide member 206 is adapted for engaging inside a slit 412 in the first part 400, and is dimensioned such that when it engages inside the slit 412, part of it extends through the slit 412 and inside into the inside of the first part 400.

Figure 3A:
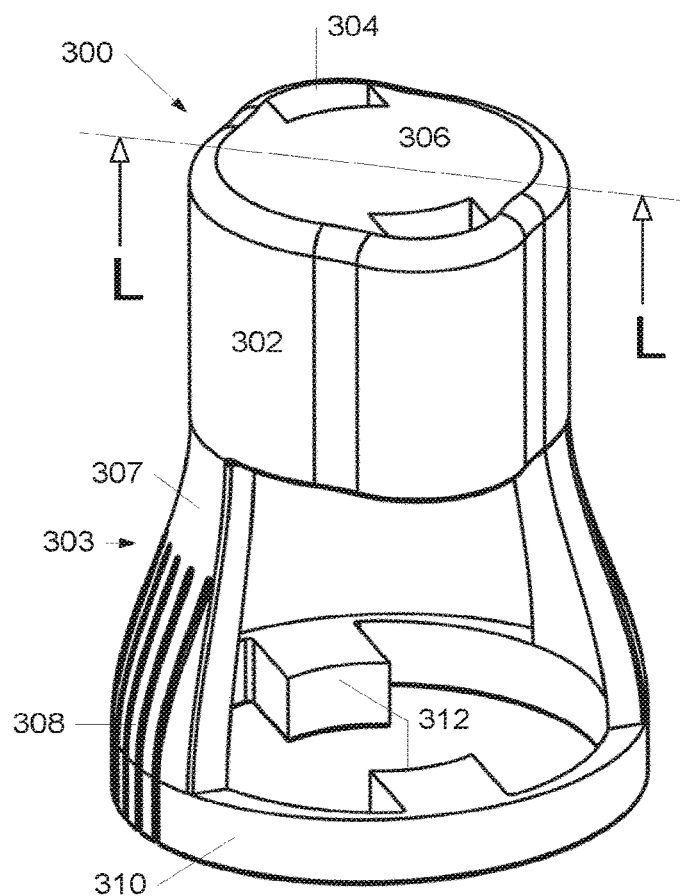
FIGS. 3A-B show the outer part of the inserter device.
Figure 3B:
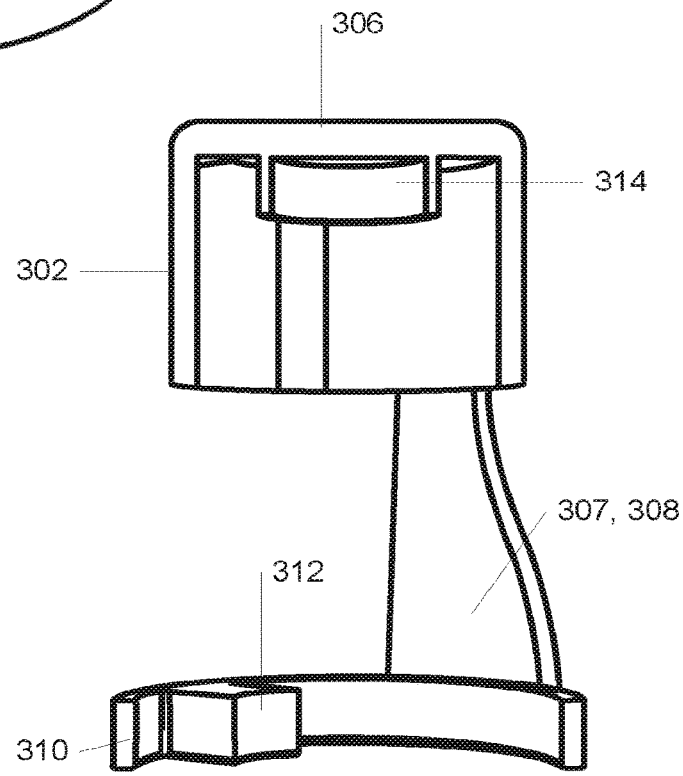

FIG. 3A shows the outer part 300 in a front on view and FIG. 3B shows the outer part 300 in a cut-through view along the axis L-L. The outer part 300 constitutes a first section 302 and a second section 303. The first section 302 comprises two openings 304 at the distal end 306 of the first section 302. The two openings 304 are adapted for engaging with the corresponding proximal protrusions 202 of the housing 200, thereby interlocking the housing 200 and the outer part 300. On the inside of the distal end 306 there is a protruding annular collar 314 where around the distal end of the insertion spring 402 is positioned. This ensures that the insertion spring 402 cannot be displaced horizontally before, during and/or after insertion and/or retraction of the insertion needle 102.

The second section 303 comprises two outwardly extending arms 307, an engaging device 310, release elements 308, and locking elements 312. The extending arms 307 are positioned opposite one another in the horizontal plane and are directly attached to the first section 302 at their distal end. The engaging device 310 is in this embodiment a ring, which can be either circular or oval. Other shapes could also be imagined. The release elements 308 extend partly on the outwardly extending arms 307 and partly on the engaging device 310.

The locking elements 312 are in this embodiment two inwardly pointing parts for engaging with the openings 204 in the housing 200. The locking elements 312 are positioned opposite one another on the engaging device 310 and are displaced approximately 90 degrees in relation to the release elements 308 and the arms 303. The locking elements 312 ensures that the insertion spring 402 stays in a pre-loaded position before activation of the inserter device 100 by engaging with locking members 410 on the first part 400, thereby fixing the first part 400 at the top of the distal end 205 of the housing 200, thus at a position on top of the locking elements 312.

Figure 4A:
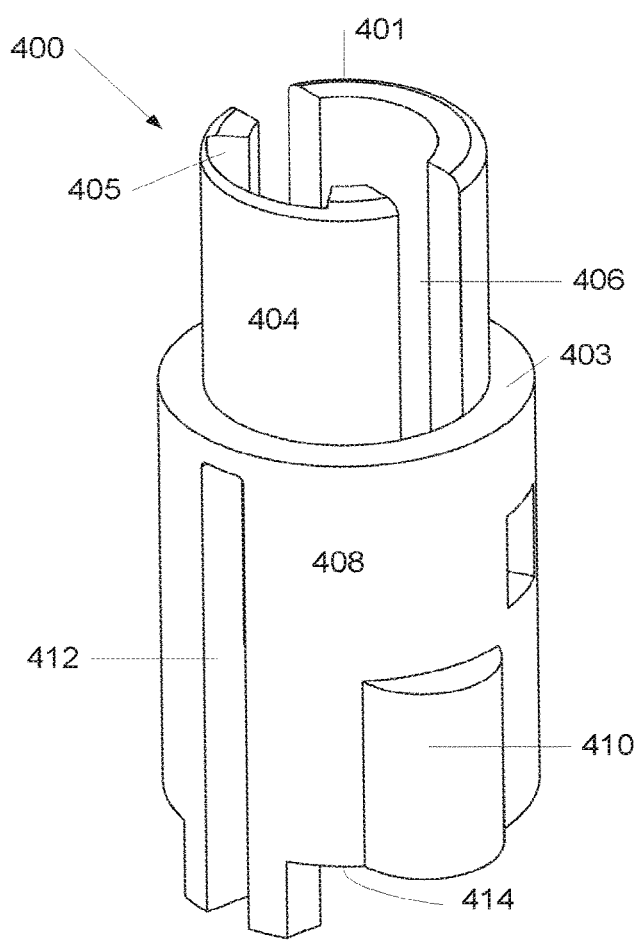
FIGS. 4A-C show the first part of the inserter device.
Figure 4B:
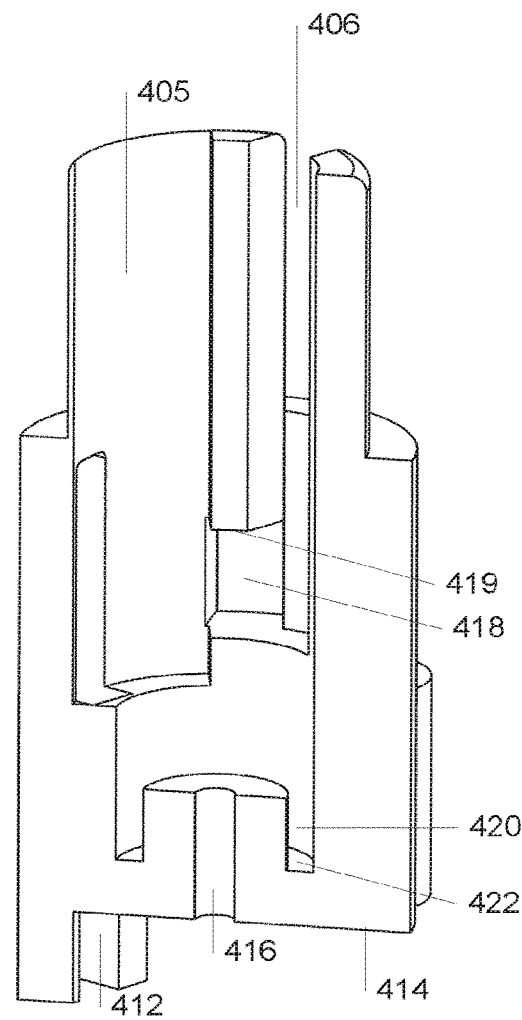
Figure 4C:
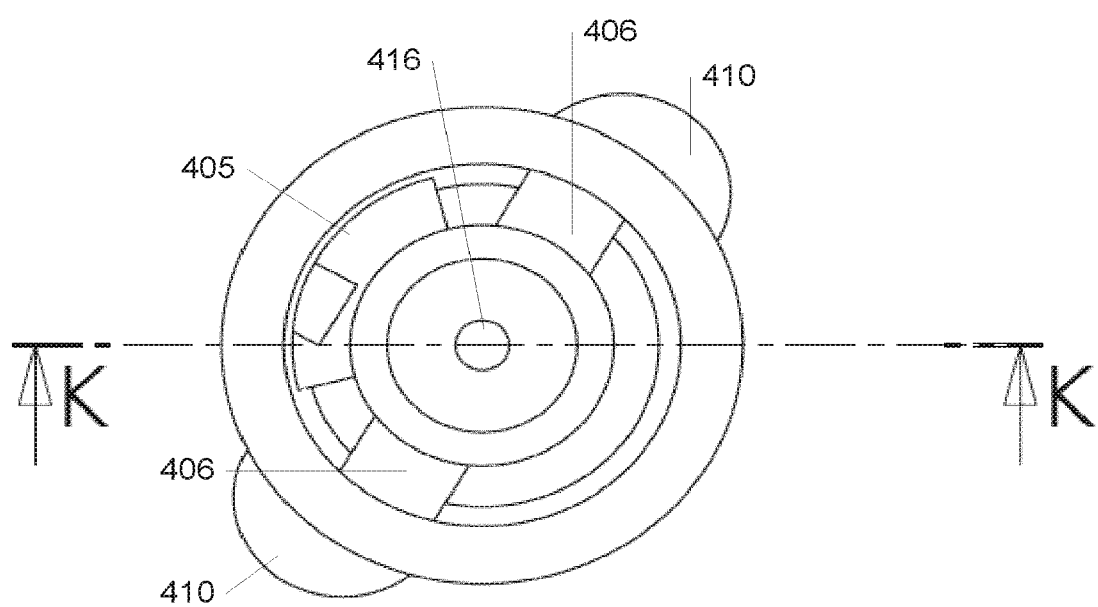

FIG. 4A shows the first part 400 in a front view; FIG. 4B shows the first part 400 in a cut-through view along the axis K-K; shows and FIG. 4C shows the first part 400 in view from the distal end 401 of the first part 400. The first part 400 constitutes a tube comprising a first section 404 and a second section 408, where the outer diameter of the first section 404 is smaller than the outer diameter of the second section 408, thereby forming a support surface 403, whereupon the insertion spring 402 rests at one end.

The first section 404 comprises two releasing slits 406 for engaging with corresponding locking members 508, 508' on the second part 500. The releasing slits 406 extends from the distal end 401 to the distal surface 407 of the proximal end 409 along a vertical axis parallel to the insertion direction. The first section 404 further comprises a recess 405 on the inner surface facilitating space for an inclining guide member 510 on the second part 500.

The second section 408 has locking members 410 (in this embodiment two protrusions) placed opposite one another in the horizontal plane on the outside of the second section 408. In the pre-loaded shelf position shown in FIG. 7, the locking members 410 are engaging with the locking elements 312 of the outer part 300. This secures the insertion spring 402 in the pre-loaded position preventing the insertion needle 102 from being activated during transportation. Between the two locking members 410 is a slit 412 for receiving the inner housing guide member 206 of the housing 200 during activation of the inserter device 100.

The proximal surface 414 of the first part 400 is provided with a central annular opening 416 (see FIG. 7) where through the insertion needle 102 can pass when inserting the subcutaneous part 106 in a patient. The opening 416 is normally so small that it only allows the insertion needle 102 to pass through, thus the diameter of the opening 416 is normally 10-20% larger than the diameter of the insertion needle 102. This is advantageous as it is prevents a user from accidently putting a finger through the opening 416 and e.g. get in contact with the used insertion needle 102. Further, by having a very small opening 416, the insertion needle 102 is hardly visible, which has a positive psychological effect on patients/users that are afraid of needles.

On the inside of the second section 408 are found openings 418 for engaging with corresponding locking members 508, 508' on the second part 500. In the shelf and the insertion position, the locking members 508, 508' on the second part 500 are supported by a support rim 419, thereby fixing the retraction spring 502 and the second part 500 in the pre-loaded state. On the distal surface 422 of the proximal end 421 is an annular recess 420 (see FIG. 7) accommodating one end of the retraction spring 502, thereby ensuring that it cannot be displaces horizontally before, during and/or after insertion and/or retraction.

Upon insertion of the insertion needle 102, the proximal surface 414 exercises a pressure on the subcutaneous part 106 locking the subcutaneous body part 110 inside a cavity of the port site 104. Further, as the first part 400 after insertion of the insertion needle 102 is pressing against the distal surface 114 of the subcutaneous part 106 due to the relaxed insertion spring 402, the proximal surface 414 assists in releasing the subcutaneous part 106 from the insertion needle 102 as the insertion needle 102 is extracted into the inserter device 100.

Optionally, the first part 400 can be provided with additional means for releasing the subcutaneous part 106 from the insertion needle 102. These means for releasing the subcutaneous part 106 can have the form of a distance piece, which assures that the subcutaneous part 106 is pushed down into the opening of the base 104 with such a force that the subcutaneous part 106 can get past or get in contact with a locking mechanism inside the opening of the base 104. In one embodiment, the means for releasing the subcutaneous part 106 comprises a flat spring placed between the proximal surface 414 of the first part 400 and the distal surface 114 of the subcutaneous part 106. The flat spring is attached to or is a part of the first part 400 at one end. As the first part 400 is pushed down towards the base 104 by the insertion spring 402, the flat spring will be loaded as the first part 400 gets close enough to the base 104. The flat spring will then exercise a pressure on the subcutaneous part 106 locking the subcutaneous body part 100 inside the opening of the base 104.

FIG. 5A shows the second part 500 in a front view and FIG. 5B the second part 500 in a cut-through view along the axis connecting the locking members 508, 508'. The second part 500 constitutes a small elongated tube which can fit inside the first part 400. The second part 500 comprises a first section 504 and a second section 506, where the outer diameter of the first section 504 is larger than the diameter of the second section 506, thereby accommodating a support surface 503 for one end of the retraction spring 502 as shown in FIGS. 10C and 11C, which ensures that the retraction spring 502 remains positioned around the second section 506 at one end at all times.

On the outside of the first section 504 are locking members 508, 508' (in this embodiment two protrusions) which slide inside the corresponding releasing slits 406 in the first part 400 during activation of the inserter device 100. In between the locking members 508, 508' is the inclining guide member 510. The second part 500 further comprises recesses 512 for guiding the second part 500 in position inside the first part 400 during manufacturing of the inserter device 100. The insertion needle 102 is attached to the second part 500 and extends up inside the normally solid second part 500.

The position of the second part 500 inside the first part 400 is only an embodiment of the invention. The reverse could also be imagined.

FIG. 6 shows an embodiment of the port site 104 being an infusion port wherein the subcutaneous part 106 comprises a cannula 108 and a body part 110. The body part 110 is shaped such that it secures the subcutaneous part 106 in the port site 104 upon insertion of the subcutaneous part 106 in a patient's skin 112. The subcutaneous part 106 is positioned on the insertion needle 102 and is kept in position due to the friction between the insertion needle 102 and the soft contact parts of the subcutaneous part 106 such as the cannula 108. The insertion needle 102 can be located inside, alongside or outside the cannula 108.

In some embodiments, one or more surfaces of the port site 104 and/or the subcutaneous part 106 include an antimicrobial coating 116 positioned thereon. The antimicrobial coating 116 may comprise one or more antimicrobial materials, e.g., a hydrophilic material, a silver (Ag) or silver chloride (AgCl) material, a hydrogel material, a hydrophilic material incorporated into a thermoplastic elastomer (TPE), and a material including nanoparticles incorporated into polymer structures and configured to sterilize the polymers when exposed to UV light. For example, the antimicrobial coating 116 may include any one or more of the polymers or polymer mixtures described in U.S. Pat. Nos. 9,186,438 and 10,058,638, each of which are incorporated herein by reference in their entireties.

In some embodiments, the hydrophilic material includes an amphiphilic phosphorylcholine polymer (e.g. PC1036). The hydrophilic material may include other phosphorylcholine or other phospholipid materials as well. In some embodiments, the hydrophilic material includes, e.g., polyvinyl chloride (PVC) plasticized with dioctyl terephthalate (bis(2-ethylhexyl) benzene-1,4-dicarboxylate or di(2-ethylhexyl) terephthalate, (DOTP) or (DEHT), respectively. In some embodiments, the hydrophilic material incorporated into a TPE includes a polyolefin based synthetic thermoplastic polyolefin elastomer containing a hydrophilic additive.

In some embodiments, the hydrogel material includes polyvinylpolypyrrolidone (PVPP) and/or polyvinylpyrrolidone (PVP). In some embodiments, the silver or silver chloride material may be any one or more of those described in U.S. application Ser. No. 11/194,951 and U.S. Pat. No. 6,451,003, each of which are incorporated herein by reference in their entireties.

Figure 7:
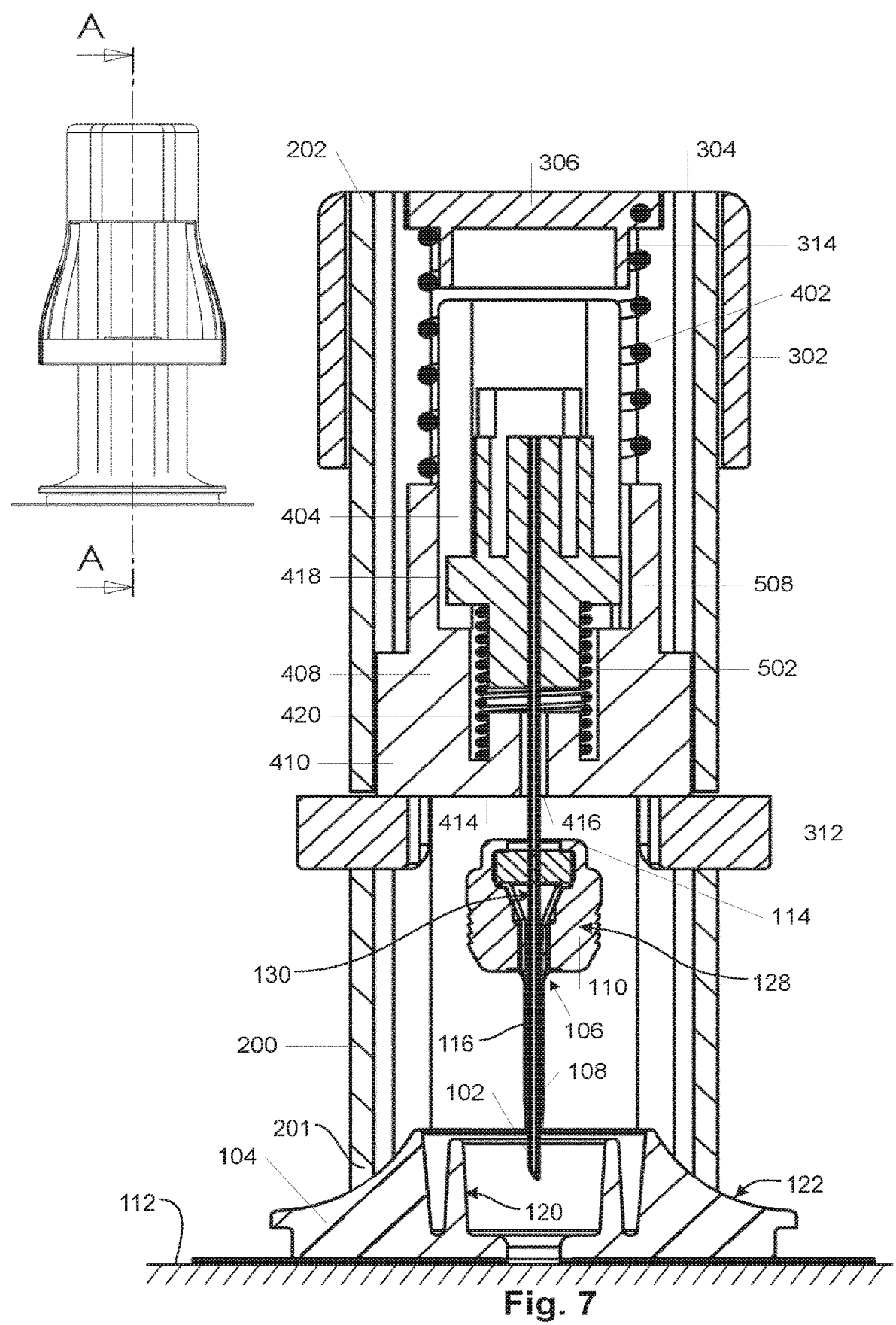
FIG. 7 shows a cut-through view of the inserter device in a shelf position.
Figure 8:
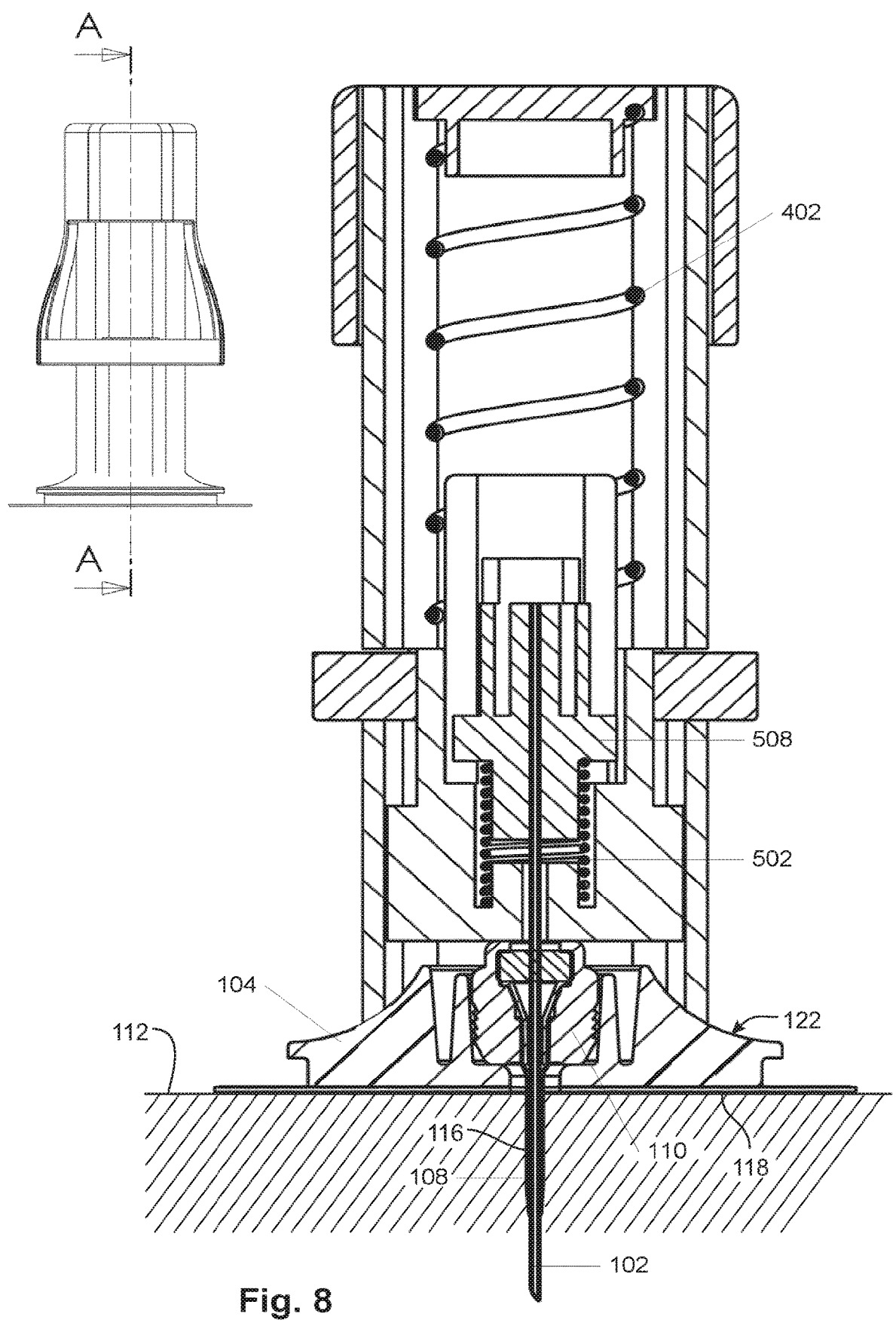
FIG. 8 shows a cut-through view of the inserter device in an inserted position.
Figure 9:
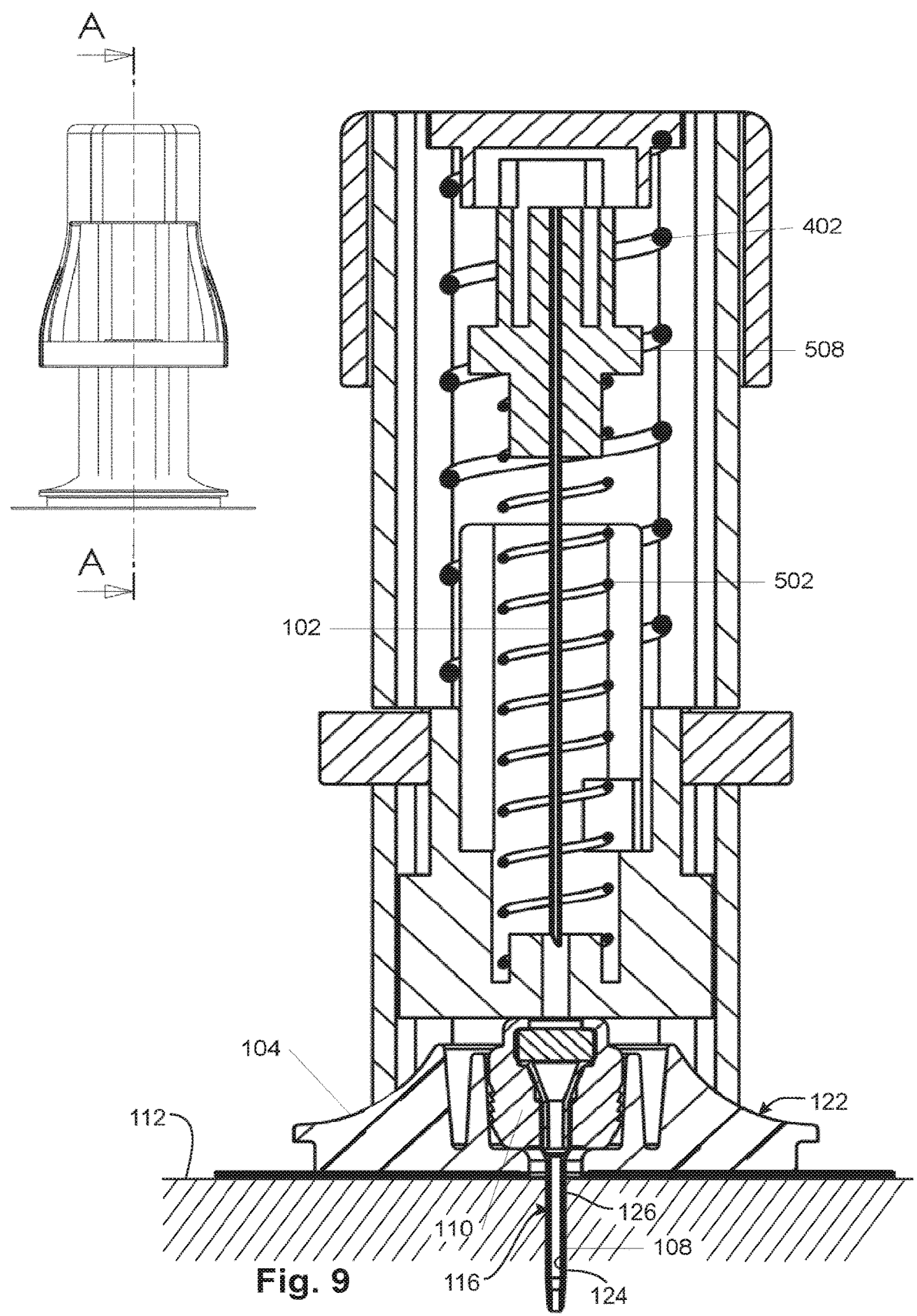
FIG. 9 shows a cut-through view of the inserter device in a retracted position.

In FIGS. 7-9, the inserter device 100 is displayed in a cut-through view along line AA. In here, the different parts 200, 300, 400, 500 interlocking with one another can be seen more clearly.

Normally, the four parts constituting the inserter device 100, i.e. the housing 200, the outer part 300, the first part 400, and the second part 500, are constructed from a hard plastic possibly combined with sections of a softer material preventing the parts from breaking during activation of the inserter device 100. The insertion spring 402 and the retraction spring 502 are normally metal springs, but other types of materials such as e.g. plastic could also be used.

FIG. 7 shows the inserter device 100 in a shelf state before activation of the inserter device 100. Both springs 402, 502 are in a pre-loaded position. The insertion spring 402 and first part 400 are secured in the pre-loaded shelf position by the locking elements 312 preventing the first part 400 from being displaced in relation to the housing 200. The second part 500 is kept in the pre-loaded shelf position by the locking members 508, 508', which are engaging with the two openings 418 and the support rim 419 on the inside of the first part 400.

The pre-loading of the two springs 402, 502 in the shelf state ensures an advantageous compact design of the inserter device 100.

FIG. 8 shows the inserter device 100 in the inserted position where the cannula 108 has been inserted into the patient's skin 112 and the body part 110 is secured inside the port site 104. The port site 104 includes a proximal surface 118 configured to contact the patient's skin 112. In some embodiments, the antimicrobial coating 116 is positioned on the proximal surface 118 of the port site 104.

As shown in FIG. 7, the port site 104 includes a plurality of inner surfaces 120 and a plurality of outer surfaces 122. The plurality of inner surfaces 120 includes the surfaces which are arranged to surround the body part 110 when the body part 110 is inserted in a cavity of the port site 104. The plurality of inner surfaces 120 further includes the surfaces which define an opening in the port site 104 through which the cannula 108 is configured to extend. The remaining surfaces of the port site 104 define the plurality of outer surfaces 122 (including the proximal surface 118). The antimicrobial coating 116 may be positioned on any one or more of the surfaces included in plurality of inner surfaces 120 and the plurality of outer surfaces 122 of the port site 104.

Referring now to FIG. 9, the cannula 108 includes an inner surface 124 and an outer surface 126. The inner surface is configured to contact the insertion needle 102 to maintain the insertion needle 102 in position due to the friction therebetween as described above. The outer surface 126 is positioned opposite the inner surface 124. The antimicrobial coating 116 may be positioned on one or both of the inner surface 124 and the outer surface 126 of the cannula 108.

As shown in FIG. 7, the body part 110 may include a plurality of outer surfaces 128 including a ribbed portion configured to maintain the body part 100 within the cavity of the port site 104. Further, the body part 110 may include a plurality of inner surfaces 130 configured to receive an external device such as an injection needle or a supporting structure thereof. The antimicrobial coating 116 may be positioned on any one or more of the surfaces included in plurality of inner surfaces 130 and the plurality of outer surfaces 128 of the body part 110.

In some embodiments, the port site 104 includes an adhesive surface, which is used for attaching the port site 104 releasably to the patient's skin 112. A release paper has to be removed from the port site 104 prior to placing it on the patient's skin 112. In such embodiments, the adhesive material may be included in the antimicrobial coating 116 or may be separate and/or distinct from the antimicrobial coating 116.

In the inserted position shown in FIG. 8, the insertion needle 102 is still inserted in the patient, thus it has not returned to a retracted position yet. The insertion spring 402 is in a relaxed position, whereas the retraction spring 502 is still in the pre-loaded position.

FIG. 9 shows the inserter device 100 in a retracted position after the cannula 108 has been inserted into the patients skin 112 and the insertion needle 102 attached to the second part 500 has been retracted to a position at the distal end 205 of the housing 200, i.e. no longer positioned inside the first part 400. The retraction spring 502 is in the relaxed position from where it cannot be re-loaded again without breaking apart the inserter device 100. This ensures that the insertion needle 102 is contained inside the inserter device 100 unable to extend out of it.

Insertion of the subcutaneous part 106 into a patients skin 112 is done by placing the inserter device 100 on the patients skin 112 with the port site 104 positioned directly on top of the patients skin 112, and then activating the inserter device 100. Normally, a protective release paper has to be removed from the port site 104 prior to placing it on the patients skin 112, thereby exposing an adhesive layer underneath the port site 104 for fastening the port site 104 to the patients skin 112.

Activation of the inserter device 100 is done by applying a pressure on the two release elements 308 on the outer part 300, i.e. deforming the engaging device 310 by pressing the two release elements 308 closer together. The distance between the locking elements 312 thereby increases such that there is enough space to allow for the locking members 410 on the first part 400 to pass by the locking elements 312 at the aid of the insertion spring 402, the latter which in this manner is allowed to relax.

The clock-wise turning of the second part 500 prompt by the housing guide member 206 progressing inside the slit 412 and turning the inclining guide member 510 is observable when comparing FIGS. 10A-C and FIGS. 11A-C, in particular the FIGS. 10A-B and FIGS. 11A-B. The release of the locking members 508, 508' from the inner openings 418 is seen most clearly in the FIGS. 10C and 11C, where FIG. 10C shows the locking members 508, 508' being secured underneath the inner openings 418, and FIG. 11C shows the locking members 508, 508' positioned in the releasing slits 406 in first part 400, allowing the retraction spring 502 to relax and thereby push the second part 500 to an extracted position, where it is no longer contained inside the first part 400.

The second part 500 is normally turned 10-40 degrees in relation to the first part upon release of the second part 500 form the first part 400.

The inserter device 100 is constructed such that it can only be used once, since it is impossible to re-load the springs 402, 502 after activation of the inserter device 100. This is advantageous as the user cannot be tempted to use the device more than once and thereby expose himself/herself to an unnecessary health risk.

Construction of the inserter device 100 from essentially four interconnected parts 200, 300, 400, 500 combined with two springs 402, 502 and an insertion needle 102 allows for a simple construction, whereby a rather compacted device is obtained. This reduces production costs.

Normally, the inserter device 100 is contained in a protective bag during transportation. The conditions inside the bag are sterile ensuring that the inserter device 100 can be kept sterile up until the time where it is going to be used. The only time, the inserter needle 102 is exposes is in the brief moment of insertion. This makes the inserter device 100 safe to handle as the user cannot get in contact with the insertion needle 100 prior to activation of the device and/or after the automatic retraction of the insertion needle 100. It is thereby safe to dispose the inserter device 100 along with ordinary household waste without protecting it before hand.

The automatic insertion and automatic retraction of an insertion needle 102, prompted by applying a pressure in the horizontal plane, is easy to perform by the user, since it essentially involves one action. Further, as the insertion process does not involve applying a pressure in the direction towards to skin, the procedure is more appealing to users that have a fear of injection needles and other penetrating devices, as these users often find it significantly more difficult to insert an insertion needle if they have to apply a pressure towards the skin at the same time.

While this disclosure has been described with respect to at least one embodiment, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. An inserter system comprising:
   a medical device and an inserter device for subcutaneously inserting at least a portion of the medical device,
   the medical device including an antimicrobial coating, the medical device comprising: 1) a port site having a cavity with the antimicrobial coating positioned on the cavity, the port site including a plurality of outer surfaces and a plurality of inner surfaces, and 2) a subcutaneous part, including a plurality of outer surfaces and a plurality of inner surfaces, the subcutaneous part being securable to the port site, wherein the subcutaneous part includes a body part having a ribbed portion with the antimicrobial coating positioned on the ribbed portion and wherein the ribbed portion is configured to maintain the body part within the cavity, and a cannula, wherein one or more of the plurality of inner surfaces and one or more of the plurality of outer surfaces of the port site and one or more of the plurality of inner surfaces and one or more of the plurality of outer surfaces of the subcutaneous part includes the antimicrobial coating positioned on the one or more of the plurality of inner surfaces of the port site on the one or more of the plurality of outer surfaces of the port site, on the one or more of the plurality of inner surfaces of the subcutaneous part, and on the one or more of the plurality of outer surfaces of the subcutaneous part, and the inserter device comprising:
      an outer part comprising one or more locking elements including a first locking element and one or more release elements including a first release element;
      a housing; and
      a functional part accommodated in the housing;
      wherein the housing comprises a sidewall with an inner surface forming a cavity, the housing extending from a first end to a second end along a first axis and comprising one or more housing guide members including a first housing guide member for engagement with one or more guide members of the functional part, and where the housing is at least partly covered by the outer part;
      wherein the functional part comprises:
         a first part with a first body extending from a first end to a second end along the first axis, the first part comprising one or more first locking members;
         a second part releasably connected to the first part and comprising a second body extending from a first end to a second end along the first axis, the second part comprising a second guide member and one or more second locking members;
         an insertion needle attached to the second part;
         an insertion spring adapted for moving the first part from a first position to a second position in an insertion direction along the first axis in relation to the housing; and
         a retraction spring adapted for moving the second part from the second position to a third position in an extraction direction along the first axis in relation to the housing;
      wherein the first housing guide member and the second guide member are configured for rotating the second part about the first axis when the first part is moved from the first position to the second position, whereby the second part is moved from a locked position to an unlocked position relative to the first part, and
      wherein the inserter system includes a shelf state before activation of the inserter system wherein the body part is not located in the cavity of the port site, and an inserted position where the cannula is inserted into a patient's skin in which the body part is located in the cavity of the port site and the body part is configured to secure the subcutaneous part to the port site.

2. The inserter system according to claim 1, wherein the first locking element is two protrusions positioned on an annular engaging device extending inwards.

3. The inserter system according to claim 2, wherein the first release element is two surfaces positioned on the annular engaging device.

4. The inserter system according to claim 2, wherein the one or more first locking members are protrusions on an outer surface of the first part.

5. The inserter system according to claim 1, wherein the first housing guide member is a wall extending from the sidewall into the cavity of the housing.

6. The inserter system according to claim 1, wherein the second guide member is an inclining sidewall extending outwardly from an outer surface of the second part.

7. The inserter system according to claim 1, wherein the one or more second locking members are protrusions extending outwardly from an outer surface of the second part.

8. The inserter system according to claim 1, wherein the outer part comprises an annular collar on an inside of the outer part; wherein the insertion spring at a first end encircles the annular collar; and wherein the insertion spring at a second end encircles an outer part of the first part.

9. The inserter system according to claim 1, wherein the retraction spring at a second end encircles an outer part of the second part; and wherein the first part comprises an annular recess on an inside of the first part for supporting the retraction spring at a first end.

10. The inserter system according to claim 1, wherein the subcutaneous part is configured to be secured inside the cavity in the port site upon the subcutaneous insertion of the medical device.

11. The inserter system according to claim 10, wherein the first part when in the second position exercises a pressure on the subcutaneous part thereby locking the subcutaneous part inside the cavity in the port site; and
    wherein the first part when the second part is in the third position exercises a pressure on the subcutaneous part thereby preventing the subcutaneous part from departing from the port site upon extraction of the insertion needle.

12. The inserter system according to claim 10, wherein the first part when the second part is in the third position exercises a pressure on the subcutaneous part thereby preventing the subcutaneous part from departing from the port site upon extraction of the insertion needle.

13. The inserter system according to claim 1, wherein the antimicrobial coating comprises an amphiphilic phosphorylcholine polymer.

14. The inserter system according to claim 1, wherein the cannula extends proximally from the body part, wherein an inner surface and an outer surface of the cannula includes the antimicrobial coating, and the ribbed portion includes one or more of the plurality of outer surfaces of the subcutaneous part and includes one or more of the plurality of inner surfaces of the subcutaneous part.

15. The inserter system according to claim 1, wherein the port site includes a proximal surface including at least one of the plurality of outer surfaces of the port site, the proximal surface configured to contact the patient's skin when the medical device is subcutaneously inserted; and wherein the antimicrobial coating is positioned on the proximal surface of the port site.

16. An inserter system comprising:

a medical device including an antimicrobial coating, the medical device including a port site including a cavity with the antimicrobial coating, the port site having a plurality of outer surfaces and a plurality of inner surfaces, a subcutaneous part securable to the port site, the subcutaneous part including a body part having a ribbed portion with the antimicrobial coating positioned on the ribbed portion and wherein the ribbed portion is configured to maintain the body part within the cavity, the subcutaneous part including a plurality of outer surfaces and a plurality of inner surfaces, and an inserter device for subcutaneously inserting at least a portion of the medical device;

wherein each of the plurality of inner surfaces of the port site, each of the plurality of outer surfaces of the port site, each of the plurality of inner surfaces of the subcutaneous part, and each of the plurality of outer surfaces of the subcutaneous part includes the antimicrobial coating positioned on each of the plurality of inner surfaces and each of the plurality of outer surfaces of the port site and on each of the plurality of inner surfaces and each of the plurality of outer surfaces of the subcutaneous part; and wherein the inserter device comprises:

an outer part comprising one or more locking elements including a first locking element and one or more release elements including a first release element;

a housing; and a functional part accommodated in the housing;

wherein the housing comprises a sidewall with an inner surface forming a cavity, the housing extending from a first end to a second end along a first axis and comprising one or more housing guide members including a first housing guide member for engagement with one or more guide members of the functional part, and where the housing is at least partly covered by the outer part;

wherein the functional part comprises:

a first part with a first body extending from a first end to a second end along the first axis, the first part comprising one or more first locking members;

a second part releasably connected to the first part and comprising a second body extending from a first end to a second end along the first axis, the second part comprising a second guide member and one or more second locking members;

an insertion needle attached to the second part;

an insertion spring adapted for moving the first part from a first position to a second position in an insertion direction along the first axis in relation to the housing; and a retraction spring adapted for moving the second part from the second position to a third position in an extraction direction along the first axis in relation to the housing;

wherein the first housing guide member and the second guide member are configured for rotating the second part about the first axis when the first part is moved from the first position to the second position, whereby the second part is moved from a locked position to an unlocked position relative to the first part, and wherein the inserter system includes a shelf state before activation of the inserter system wherein the body part is not located in the cavity of the port site, and an inserted position where a cannula of the subcutaneous part is inserted into a patient's skin in which the body part is located in the cavity of the port site and the body part is configured to secure the subcutaneous part to the port site.

17. The inserter system according to claim 16, wherein the antimicrobial coating comprises an amphiphilic phosphorylcholine polymer.

\* \* \* \* \*